(12) United States Patent
Yotoriyama (10) Patent No.: US 8,187,542 B2
(45) Date of Patent: May 29, 2012

(54) OPTICAL DETECTION FIELD HAVING DIAMOND-LIKE CARBON THIN FILM FORMED THEREIN

(75) Inventor: Tasuku Yotoriyama, Tokyo (JP)

(73) Assignee: Sony Corporation, Tokyo (JP)

( * ) Notice: Subject to any disclaimer, the term of this patent is extended or adjusted under 35 U.S.C. 154(b) by 58 days.

(21) Appl. No.: 12/394,347

(22) Filed: Feb. 27, 2009

(65) Prior Publication Data

US 2009/0263807 A1    Oct. 22, 2009

(30) Foreign Application Priority Data

Feb. 29, 2008 (JP) ................. P2008-050312

(51) Int. Cl.
*G01N 21/00* (2006.01)
(52) U.S. Cl. .................. 422/82.05; 422/400; 422/425; 422/68.1

(58) Field of Classification Search ............. 422/400, 422/425, 68.1, 82.05
See application file for complete search history.

(56) References Cited

U.S. PATENT DOCUMENTS 6,749,813 B1 *  6/2004  David et al. ............. 422/502

FOREIGN PATENT DOCUMENTS

| JP | 6-323847 | 11/1994 |
|---|---|---|
| JP | 2004-45201 | 2/2004 |
| JP | 2005-345181 | 12/2005 |
| JP | 2005-345279 | 12/2005 |
| JP | 2005345279 | * 12/2005 |
| JP | 2006-322813 | 11/2006 |

* cited by examiner

*Primary Examiner* — Jill Warden
*Assistant Examiner* — Monique Cole
(74) *Attorney, Agent, or Firm* — Finnegan, Henderson, Farabow, Garrett & Dunner, L.L.P.

(57) ABSTRACT

An optical detection field, wherein a diamond-like carbon thin film containing therein fluorine is formed on a surface facing an existence region of a substance.

3 Claims, 11 Drawing Sheets

DLC
(+)
S/N=2.3

FIG.10A

DLC
(−)
S/N=1.5

OPTICAL DETECTION FIELD HAVING DIAMOND-LIKE CARBON THIN FILM FORMED THEREIN

CROSS REFERENCES TO RELATED APPLICATIONS

The present invention contains subject matter related to Japanese Patent Application JP 2008-050312 filed in the Japanese Patent Office on Feb. 29, 2008, the entire contents of which being incorporated herein by reference.

BACKGROUND OF THE INVENTION

1. Field of the Invention

The present invention relates to an optical detection field for optically detecting a substance, and more particularly to an optical detection field in which a diamond-like carbon thin film containing therein fluorine is formed on a surface facing an existence region of a substance.

2. Description of Related Art

At present, in a field of a molecular biology, it is generally carried out to detect a substance such as a nucleic acid or protein by using a fluorescent labeling reagent.

In a real time PCR (Polymerase Chain Reaction) for measuring gene representation, for example, a fluorescent labeling reagent is taken in a DNA (Deoxyribonucleic Acid) which is amplified by a PCR reaction, and the amplified DNA containing the fluorescent labeling reagent up-taken therein is fluorometrically detected, thereby monitoring the amplification of the DNA in real time.

In addition, in a DNA chip used in an exhaustive gene expression analysis, cDNA (Complementary Deoxyribonucleic Acid) synthesized from mRNA (Messenger Ribonucleic Acid) of a cell or a tissue is labeled with a fluorescent reagent, and is then hybridized with probe oligonucleotide solid-phased on a surface of a substrate. Also, a labeling reagent is fluorometrically detected, thereby detecting a substance obtained by hybridizing cDNA and probe oligonucleotide with each other.

Heretofore, the real-time PCR has been carried out by using a tube or multi-plate made of either polypropylene or polycarnonate. However, there is encountered such a problem that since a surface of a vessel made of such a plastic has a high substance adsorptive property, a nucleic acid or an enzyme adsorbs on the surface of the vessel, thereby reducing an analysis precision. In order to prevent this problem from being encountered, it is carried out that about 0.1% bovine serum albumin (BSA) or the like is added to a reaction liquid solution, and thus the adsorption of the nucleic acid or the enzyme is suppressed by utilizing competitive adsorption of the BSA on the surface of the vessel. The suppression of the adsorption of the nucleic acid or the enzyme by the competitive adsorption is generally called "blocking."

In addition, in the DNA chip as well, when the nucleic acid fluorometrically labeled with the fluorescent reagent nonspecifically adsorbs on a surface of a glass substrate, a signal-to-noise (S/N) ratio is reduced. As a result, a problem is caused in the reliability of the analysis results.

For this reason, there has been desired a technique for effectively controlling the adsorption of the substance on the surface of the vessel such as the tube or the multi-plate, or on the surface of the substrate such as a slide glass in the optical detection system such as the real-time PCR or the DNA chip.

In order to cope with this situation, the applicant of the present embodiment discloses a bioassay substance which can effectively prevent the nonspecific adsorption of a substance on a detection surface in Japanese Patent Laid-Open No. 2005-345181 (hereinafter referred to as Patent Document 1). With the bioassay substance, a carbon compound layer laminated on the substrate is modified with a functional group such as a carboxyl group charged with a negative charge, whereby a substance, charged with the negative charge, existing a reaction region can be effectively prevented from nonspecifically adsorbing on a surface in the reaction region by electrical repulsion.

It is described in Patent Document 1 that the carbon compound layer described above is made of either diamond or diamond-like carbon, and has an optical transparency for measurement of a fluorescence intensity.

Here, a diamond-like carbon thin film (hereinafter referred to as "a DLC thin film") will be described as a technique relating to the present embodiment.

The DLC thin film can be formed by utilizing either a chemical vapor deposition method such as a thermal CVD method or a physical vapor deposition method such as an ion plating method. The DLC thin film has high surface smoothness and exhibits excellent tribology (friction and abrasion) because it has a dense amorphous structure. In addition, the DLC thin film has the properties such as a high coefficient of thermal conductivity, a high insulation withstanding property, heat resistance, corrosion resistance, radio-resistance, an X-ray absorption property, inertness against a chemical substance, and a negative electron affinity.

The DLC thin film has been mainly adopted in a cutting tool, a wear part and the like until now by utilizing these properties. At present, the DLC thin film is utilized in a semiconductor device, a flat panel display device, a monitoring device for monitoring a radiation ray, an X-ray or the like, a sensor device for detecting a distortion, a pressure, a temperature, a magnetic field, or the like. Moreover, in recent years, application of the DLC thin film to the molecular biology are going forward. The technique disclosed in Patent Document 1 is one of these applications of the DLC thin film.

SUMMARY OF THE INVENTION

In the bioassay substrate disclosed in Patent Document 1, the substance is prevented from nonspecifically adsorbing on the surface of the reaction region by the electrical repulsion between the negative charge of the carboxyl group with which the carbon compound layer is modified, and the substance charged with the negative charge. For this reason, there is the possibility that the electrical repulsion is weakened due to a reactive property of the carboxyl group depending on pH of the reaction liquid solution.

In the light of the foregoing, it is therefore desirable to provide an optical detection field which is capable of exhibiting an operation for stably controlling substance adsorption, thereby enhancing an optical detection sensitivity.

In order to attain the desire described above, according to an embodiment of the present embodiment, there is provided an optical detection field, in which a diamond-like carbon thin film containing therein fluorine is formed on a surface facing an existence region of a substance.

The DLC thin film containing therein fluorine is negatively charged because fluorine is higher in electronegativity than a carbon atom as a skeleton of the DLC. In addition, the negative potential of the DLC thin film becomes very stable because fluorine is more stable even in the liquid solution than the reactive functional group or a dissociable group. Moreover, the DLC thin film containing therein a fluorine group exhibits the high hydrophobic property based on a low externally induced polarizability of a C—F bond (the low dynamic polarizability).

Therefore, in the optical detection field described above, the adsorption of the substance charged with the negative charges can be effectively suppressed based on the stable negative potential of the DLC thin film. In addition, the adsorption of the hydrophobic substance can be promoted by a hydrophobic mutual interaction based on the high hydrophobic property of the DLC thin film.

According to the present embodiment, it is possible to provide the optical detection field which is capable of exhibiting the operation for stably controlling the substance adsorption, thereby enhancing the optical detection sensitivity.

DETAILED DESCRIPTION OF THE PREFERRED EMBODIMENTS

Hereinafter, an embodiment of the present invention will be described in detail with reference to the accompanying drawings. It is noted that an embodiment which will be described below is merely an example of typified embodiments of the present invention, and thus the scope of the present invention is not intended to be construed in a limiting sense.

Figure 1A:
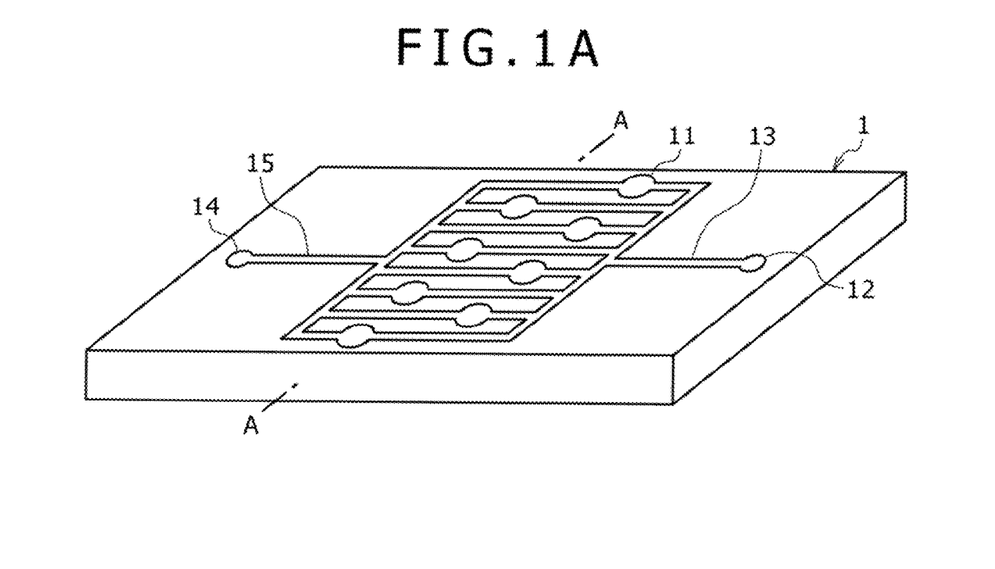
FIGS. 1A and 1B are respectively a top perspective view showing a substance for a real-time PCR in which an optical detection field according to an embodiment of the present invention is placed, and a cross sectional view taken on line A-A of FIG. 1A.
Figure 1B:
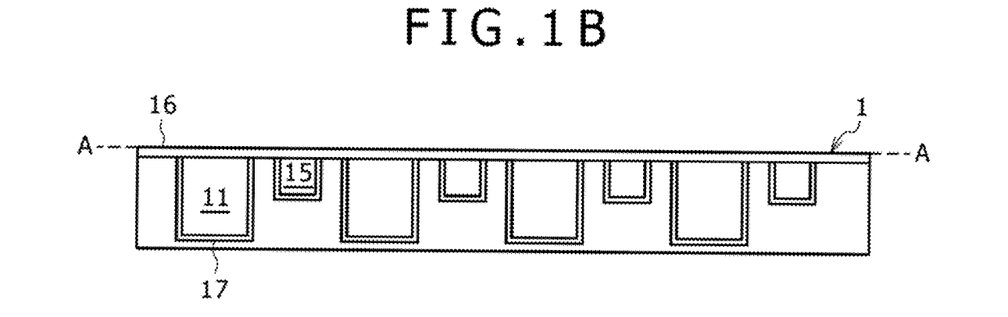

FIGS. 1A and 1B are respectively a top perspective view showing a substrate for a real-time PCR in which an optical detection field according to an embodiment of the present invention is placed, and a cross sectional view taken on line A-A of FIG. 1A. This substrate is used suitably when an exhaustive expression analysis is carried out for a plurality of genes or a plurality of specimens.

Referring now to FIG. 1A, eight reaction regions 11 in total are provided in a central portion of the substrate 1. Each of the reaction regions 11 is a field of a PCR reaction, and "an existence region of a substance" such as a target DNA, a primer, nucleotide (dNTPs), an enzyme (Polymerase), or a fluorescent labeling reagent. Thus, each of the reaction regions 11 becomes "an optical (fluorescent) detection field" as well. A DLC thin film 17 is formed on a surface of each of the reaction regions 11 (refer to FIG. 1B).

Although not especially limited, polypropylene or polycarbonate is generally used as a material for the substrate 1. In addition thereto, various plastics such as polyolefin, polyethylene, a polylactic acid, a polymethacrylic acid resin or a peak, a glass, or a metal may also be each used as the material for the substrate 1. A cover 16 for covering the substrate 1 is preferably made of a transparent material having an optical transparency for the purpose of optically detecting the fluorescent labeling reagent. It is noted that an illustration of the cover 16 is omitted in FIG. 1A (refer to FIG. 1B).

A liquid solution injecting portion 12 is provided in one end portion of the substrate 1. An introduction flow channel 13 for a reaction liquid solution is communicated with the liquid solution injecting portion 12. A side of the introduction flow channel 13 opposite to the liquid solution injecting portion 12 branches to be communicated with the individual reaction regions 11. In addition, a liquid solution extracting portion 14 is provided in the other end portion of the substrate 1. A discharge flow channel 15 for the reaction liquid solution is communicated with the liquid solution extracting portion 14. A side of the discharge flow channel 15 opposite to the liquid solution extracting portion 14 branches to be communicated with the individual reaction regions 11.

Each of the introduction flow channel 13 and the discharge flow channel 15 is a field through which the reaction liquid solution flows, and is "the existence region of the substance" such as the target DNA, the primer, dNTPs, Polymerase or the fluorescent labeling reagent. Also, the DLC thin film 17 is formed on the surface of the substance in each of the reaction regions.

It is noted that although the reaction regions 11 are provided in the eight portions in total, the number of reaction regions 11 is not especially limited. In addition, the introduction flow channel 13 and the discharge flow channel 15 are also by no means limited to the forms shown in FIGS. 1A and 1B.

Subsequently, a real-time PCR utilizing the substrate 1 will be described in brief. In this case, a description will now be given with respect to the case where "an intercalator" which is inserted and coupled between a duplex of a nucleic acid, and is excited in this state to generate a fluorescence is used as the fluorescent labeling reagent. The intercalator may be one, which is normally used, such as SYBER-Green (registered trademark), TOTO-1 or POPO-1.

Firstly, a primer set specific to a gene for which gene representation is intended to be measured is previously designed, and is then held in each of the reaction regions 11. The primer is prepared in the form of a liquid solution, and the resulting primer liquid solution is dispensed in the reaction regions 11. Or, more preferably, after completion of the dispensation, the primer liquid solution is dried once to be firmly fixed to each of the reaction regions 11.

Next, a reaction liquid solution containing therein the target DNA, the nucleotide (dNTPs), the enzyme (Polymerase), the intercalator, and a salt is injected from the liquid solution injecting portion 12. The reaction liquid solution thus injected flows through the introduction flow channel 13 to be introduced into each of the reaction regions 11. The primer which is previously held in each of the reaction regions 11 dissolves in the reaction liquid solution which has been introduced into each of the reaction regions 11.

The reaction liquid solution which has been excessively introduced into each of the reaction regions 11 flows through the discharge flow channel 15 to be discharged from the liquid solution extracting portion 14 to the outside of the substrate 1. At this time, for the purpose of preventing the primer which dissolves in the reaction liquid solution from flowing out together with the excessive reaction liquid solution, it is preferable that a moderate amount of reaction liquid solution is introduced into each of the reaction regions 11.

After completion of the introduction of the reaction liquid solution, thermal cycling is carried out for each of the reaction regions 11, thereby causing the PCR reaction to progress. The thermal cycling can be carried out under the same conditions as those in the normal PCR.

In the PCR reaction, the intercalator which has been inserted and coupled to DNA amplified from the target DNA is detected in real time, thereby measuring an amount of target DNA. The intercalator can be detected by an optical (fluorescent) detection section similar to the real-time PCR device (hereinafter simply referred to as "the device"). With regard to the optical detection section, a preferable structure thereof will be described later with reference to FIGS. 2A and 2B.

Next, the DLC film 17 formed on the surface of the substrate 1 will be described below. The DLC thin film 17 is formed on each of the surfaces of the reaction regions 11, and the surfaces of the introduction flow channel 13 and the discharge flow channel 15 (hereinafter, both the introduction flow channel 13 and the discharge flow channel 15 will be simply together referred to as "the flow channels" as well).

Since the DLC thin film contains therein fluorine, it has the negative potential based on the high electronegativity of fluorine, and the high hydrophobic property. For this reason, the surfaces of the reaction regions 11, and the surfaces of the flow channels (the introduction flow channel 13 and the discharge flow channel 15) on each of which the DLC thin film 17 is formed exhibit an operation for impeding the adsorption of the substance charged with the negative charges by the electrical repulsion. In addition, these surfaces exhibit an operation for promoting the adsorption of the hydrophobic substance by the hydrophobic mutual interaction.

In the substrate 1, the adsorption of the nucleic acid (the target DNA in this case) charged with the negative charges on each of the surfaces of the reaction regions 11, and the surfaces of the flow channels can be efficiently suppressed by the operation for impeding the adsorption of the substance charged with the negative charges on the DLC thin film 17.

In addition, in general, the protein has a hydrophobic region and a hydrophilic region. Therefore, the protein such as BSA can be efficiently adsorbed on each of the surfaces of the reaction regions 11, and the surfaces of the flow channels by utilizing the hydrophobic mutual interaction between the hydrophobic region of the protein, and the DLC thin film 17. As a result, it is possible to obtain the high blocking effect, which results in that the adsorption of the target DNA can be more effectively suppressed, and the adsorption of the primer, dNTPs, Polymerase, or the intercalator can also be suppressed.

The blocking can be carried out by injecting the liquid solution of the protein such as the BSA from the liquid solution injecting portion 12 prior to the injection of the reaction liquid solution. After completion of the blocking, the liquid solution of the protein is discharged from the liquid solution extracting portion 14 to the outside of the substrate 1. In addition, the blocking may also be previously carried out by drying the liquid solution of the protein once after being dispensed in each of the reaction regions 11.

With the existing substrate for the real-time PCR, the target DNA adsorbs on each of the surfaces of the reaction regions, and the surfaces of the flow channels. As a result, an amount of target DNA can not be precisely measured, or the fluorescence from the fluorescent labeling reagent adsorbing on each of the surfaces of the reaction regions, and the surfaces of the flow channels is detected in the form of a noise, thereby reducing the analysis precision.

On the other hand, as has been described, with the substrate 1 for the real-time PCR in which the optical detection field according to the embodiment of the present invention is placed, it is possible to effectively suppress the adsorption of the target DNA, the intercalator or the like on each of the surfaces of the reaction regions 11, and the surfaces of the introduction flow channel 13 and the discharge flow channel 15. As a result, it is possible to solve the above problem which has been caused in the related art, and thus it is possible to obtain the high analysis precision.

Such an operation for controlling the adsorption of the substance of the DLC then film can be controlled by adjusting a wettability of the DLC thin film for the water.

The wettability of the DLC thin film can be controlled based on a fluorine content rate of the DLC thin film. In the embodiment of the present invention, the fluorine content rate of the DLC thin film is set in the range of 0 to 40% in atom ratio (F/(F+C+H)), whereby a contact angle of the DLC thin film for the purified water of the DLC thin film is set at 80° or more. As a result, the preferable wettability of the DLC thin film is realized.

In the embodiment of the present invention, the DLC thin film can be structured in a way that a film thickness is in the range of 1 to 1,000 nm, and a transmittance of a visible light (a wavelength thereof is in the range of 300 to 600 nm) is set at 10% or less.

The DLC is composed of an $SP^3$ bond (diamond bond) and an $SP^2$ bond (graphite bond). When the DLC contains therein many diamond bonds, it has the high transparency. On the other hand, when the DLC contains therein many graphite bonds, it is colored with black to reduce the transparency. For this reason, the optical transparency of the DLC thin film can be controlled by adjusting a hybrid ratio, $SP^2/SP^3$, of the number of $SP^2$ bonds to the number of $SP^3$ bonds in the DLC film. In addition, the optical transparency of the DLC thin film can also be controlled by adjusting the film thickness thereof.

In the embodiment of the present invention, the hybrid ratio $SP^2/SP^3$ is set in the range of 0.5 to 1.1, and the film thickness is set in the range of 1 to 1,000 nm, thereby controlling the transmittance of the visible light in the DLC thin film at 10% or less.

As a result, with the substrate 1 for the real-time PCR in which the optical detection field according to the embodiment of the present invention shown in FIGS. 1A and 1B is placed, the leakage of the fluorescence from the reaction regions 11, and the introduction flow channel 13 and the discharge flow channel 15 is suppressed, thereby making it possible to enhance the fluorescence detection sensitivity.

Here, the effect of enhancing the fluorescence detection sensitivity by adopting the DLC thin film will be described more concretely with reference to FIGS. 2A and 2B.

Figure 2A:
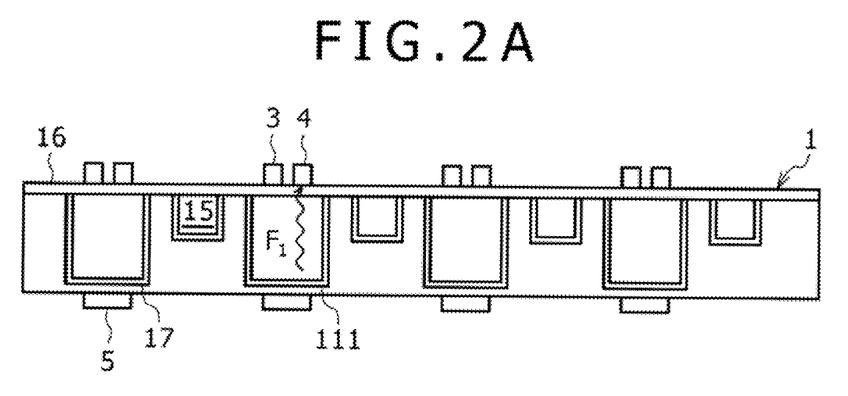
FIGS. 2A and 2B are respectively a cross sectional view showing a substrate in which the optical detection field according to the embodiment of the present invention is placed when fluorometric detection is carried out in a real-time PCR, and a cross sectional view showing an existing substance when the fluorometric detection is carried out in the real-time PCR.
Figure 2B:
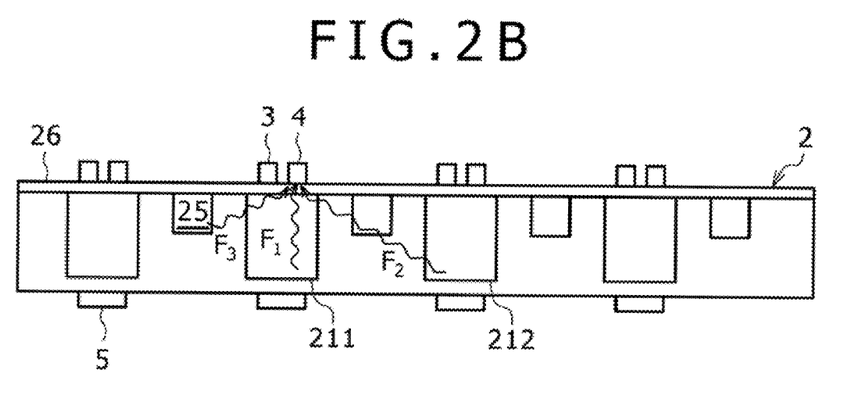

FIGS. 2A and 2B are respectively a cross sectional view showing the substrate 1 in which the optical detection field according to the embodiment of the present invention is placed when the fluorometric detection is carried out in the real-time PCR, and a cross sectional view showing an exhibiting substrate 2 when the fluorometric detection is carried out in the real-time PCR. In these figures, reference numeral 3 designates an excitation light source, and reference numeral 4 designates a fluorescence detector. Also, FIGS. 2A and 2B show the case where the fluorescence is detected by using a device in which the excitation light source 3 and the fluorescence detector 4 are provided in each of the reaction regions (optical detection field) independently of each other. Such a device is used suitably for the fluorescence detection in the substrate in which a large number of reaction regions are integrated with one another. It is noted that in FIGS. 2A and 2B, reference numeral 5 designates a temperature controlling section which will be described later.

Firstly, a factor causing the reduction of the fluorescence detection sensitivity in the existing substrate will be described with reference to FIG. 2B.

It is as previously stated that in the existing substrate 2 shown in FIG. 2B, the fluorescence from the fluorescent labeling reagent adsorbing on each of the surfaces of the reaction regions, and the surface of the discharge flow channel (or the introduction flow channel) is detected in the form of the noise, thereby reducing the analysis precision. This is remarkable in the case where in particular, a plastic such as polypropylence is used as the material for the substrate 2. In addition thereto, since the plastic has the optical transparency, the fluorescence from one reaction region may leak into another reaction region adjacent thereto.

Explaining in concrete terms, a fluorescence (refer to an arrow $F_1$, in FIG. 2B) generated from the intercalator by an excitation light from the excitation light source 3 in one reaction region 21 (designated with reference numeral 211) is detected by corresponding one of the fluorescence detectors 4. In this case, when the fluorescence leaks from another reaction region 21 (designated with reference numeral 212) adjacent to the one reaction region 21 (211) to the one reaction region 21 (211) (refer to an arrow $F_2$), this leakage fluorescence $F_2$ may be detected by the corresponding one of the fluorescence detectors 4.

When the intercalator adsorbs on the surface of the discharge flow channel 25 (or the introduction flow channel 23) communicated with the reaction region 211, the detection of such a leakage fluorescence (hereinafter referred to as "a cross-talk") may also be made between the reaction region 211 and the discharge flow channel 25 (refer to an arrow $F_3$) in FIG. 2B.

The cross-talk occurring either between the reaction regions 21, or between the reaction region 21 and the discharge flow channel 25 (or the introduction flow channel 23) is detected in the form of the noise by the fluorescence detector 4. Thus, the cross-talk becomes the factor causing the reduction of the fluorescence detection sensitivity. Moreover, in the existing substrate 2, a noise caused by the auto-fluorescence from a base material composing each of the reaction regions 21 also becomes the factor causing the reduction of the fluorescence detection sensitivity.

On the other hand, in the substrate 1 in which the optical detection field according to the embodiment of the present invention is placed as shown in FIG. 2A, it is possible to effectively inhibit the cross-talk occurring either between the reaction regions 11, or between the reaction region 11 and the discharge flow channel 15 (or the introduction flow channel 13) by controlling the optical transparency of the DLC thin film 17.

That is to say, in the substrate 1, the DLC thin film 17 having the optical transparency reduced to 10% or less is formed on each of the surfaces of the reaction regions 11, and the surfaces of the introduction flow channel 13 and the discharge flow channel 15, thereby blocking off the leakage fluorescence. As a result, no cross-talk occurs therebetween. In addition, the generation of the auto-fluorescence from the base material can also be inhibited by the DLC thin film 17 having the low auto-fluorescence property. As a result, in the substrate 1, the noise caused by the cross-talk or the auto-fluorescence from the base material is reduced, thereby making it possible to obtain the high fluorescence detection sensitivity.

Next, a description will be given with respect to the effect obtained from the high thermal conductivity which each of the temperature controlling section 5 and the DLC thin film 17 has.

The temperature controlling section 5 is provided in the device for the purpose of controlling the temperature of the PCR reaction. When the temperature controlling sections 5 are individually provided so as to correspond to the reaction regions 11, respectively, as shown in FIG. 2A, a Peltier element or the like can be suitably adopted as the temperature controlling section 5. In addition, when the temperature controlling sections 5 are not individually provided, a heat block which is normally used may be used the as the temperature controlling section 5.

Here, in general, the thermal conductivity of the plastic is about two digits lower than that of a metal, a glass, silicon, or ceramics. For this reason, the existing substrate made of a plastic involves a problem that a heating (or cooling) temperature by the temperature controlling section 5 is hardly transmitted through the reaction liquid solution within each of the reaction regions.

For this reason, it takes a lot of time for the reaction liquid crystal to reach a thermal equilibrium state. Thus, for this time period, the nonspecific gene amplification by a misannealing treatment for the primer occurs in some cases. When the intercalator is used as the fluorescent labeling reagent, since such nonspecific gene amplification is detected as the noise without being distinguished from the amplification of the target DNA, it becomes a factor reducing the measurement precision.

On the other hand, in the substrate 1 (refer to FIG. 2A) in which the optical detection field according to the embodiment of the present invention is placed, the heating (or cooling) temperature applied from the temperature controlling section 5 to the substrate 1 is speedily transmitted through the DLC thin film 17 having the excellent thermal conductivity to heat (or cool) the reaction liquid solution in each of the reaction regions 11 from a bottom surface and the side surface of each of the reaction regions 11.

As a result, it is possible to shorten a time demanded for the reaction liquid solution to reach the thermal equilibrium state. Thus, it becomes possible to enhance the measurement precision by reducing the noise caused by the misannealing for the primer. In addition, it is also possible to realize high throughput for the analysis by speeding up the reaction speed of the PCR.

The optical detection field according to the embodiment of the present invention has been described so far by giving the substrate for the real-time PCR as the example. Here, the optical detection field of the present invention is by no means limited in application to the real-time PCR, and thus can be generally adopted for optically detecting a substance.

A DNA chip is given as a preferable and concrete example. In the case of the DNA chip, cDNA synthesized from mRNA of a cell or a tissue for which the gene representation is desired to be investigated is hybridized with probe oligonucleotide solid-phased in a reaction region (an existence region of a substance) on a substrate. Thus, the fluorescence detection is carried out for the fluorescent labeling reagent with which cDNA is labeled, or the fluorescent labeling reagent (intercalator) inserted and coupled between a hybridized duplex.

In this case, the optical detection field according to the embodiment of the present invention is used as each of the reaction regions on the substrate, which results in that the adsorption of cDNA on each of the surfaces of the reaction regions, and the surfaces of the flow channels can be effectively suppressed by the adsorption impeding operation of the DLC thin film. In addition, the blocking is carried out by utilizing the hydrophobic mutual interaction of the DLC thin film, thereby making it possible to suppress the nonspecific adsorption of cDNA, the intercalator or the like.

Moreover, probe oligonucleotide solid-phased on each of the surfaces of the reaction regions of the substance can be held vertically to each of the surfaces of the reaction regions by the electrical repulsion against the DLC thin film. As a result, the efficiency of hybridizing probe oligonucleotide and cDNA with each other can be increased, thereby enhancing the analysis precision.

Therefore, as previously described by taking the real-time PCR as the example, in the DNA chip in which the optical detection field according to the embodiment of the present invention is placed, the noise caused by the cross-talk or the auto-fluorescence from the base material can be reduced, thereby obtaining the high fluorescence detection sensitivity.

The DLC thin film according to the embodiment of the present invention can be formed by utilizing the known thin film forming method such as the chemical vapor deposition method such as the thermal CVD method, or the physical vapor deposition method such as the ion plating method. However, the DLC thin film is preferably formed by utilizing a Plasma-based ion implantation and deposition (PBIID) method in which the ion implantation method and the plasma CVD method are merged with each other from a viewpoint that the DLC thin film can uniformly cover the complicated shape, and it is easy to partially add fluorine.

In the PBIID method, firstly, a raw material gas such as methane, ethane, propane, benzene, toluene, or benzyl alcohol is introduced into a chamber, and plasma is then generated within the chamber by application of a high-frequency wave or a microwave, or by D.C. discharge. Here, for example, a gas containing therein fluorine such as $C_6F_6$ or $C_6F_xH_{6-x}$ (X=1 to 6) is used singularly or with a combination thereof as the raw material gas, thereby obtaining the DLC thin film containing therein fluorine. A fluorine content rate of the DLC thin film can be controlled depending on a kind of a fluorine containing gas to be introduced, or by adjusting a partial pressure thereof. The PBIID method has the feature that a sample stage is a high-frequency antenna.

Subsequently, a minus high-frequency pulse is applied to a base material placed in the plasma, and ions are continuously accelerated, thereby depositing and forming the DLC thin film on the surface of the base material. The accelerating voltage is applied in the form of pulses. Therefore, by controlling a duty ratio between the plasma generation and the accelerating voltage, a rise in temperature of the base material can be suppressed, thereby depositing the DLC thin film at a room temperature. In addition, in this case, the hybrid ratio, $SP^2/SP^3$, of the number of $SP^2$ bonds to the number of $SP^3$ bonds ($SP^2/SP^3$) can be controlled by adjusting the accelerating voltage. It is noted that the hybrid ratio $SP^2/SP^3$ can be measured by utilizing an electron beam energy loss spectroscopy or a Raman spectroscopy.

EXAMPLES

Example 1

1. Test for Depositing DLC Thin Film

In Example 1, the DLC thin film was formed on a surface of a test substrate having reaction wells formed therein by using the PBIID method.

A polycarbonate plate 15 mm long, 25 mm in wide and 0.6 mm thick a surface on which rectangular parallelepiped-like wells each 0.5 mm in long, 0.5 mm in wide and 0.2 mm in deep were formed in 7 rows in length×7 rows in width (at well intervals of 2 mm) was used as the test substrate.

The DLC thin film was deposited by using a PBIID system (manufactured by KURITA FACTORY INC.). $C_7H_8$ was vaporized into a raw material gas, and the resulting raw material gas was introduced at a flow rate of 20 CCM into a vacuum chamber. A degree of vacuum during the film deposition was held at 1.3 Pa. For the plasma generation, a pulse width of an R.F. wave having a frequency of 13.56 MHz and a power of 500 W was set at 30 μsec. and the R.F. wave was repetitively applied at 2 kHz for 15 minutes under the conditions that an accelerating voltage was set at 2.5 kV, a pulse width was set at 5 μsec. and a delay time was set at 55 μsec.

Figure 3A:
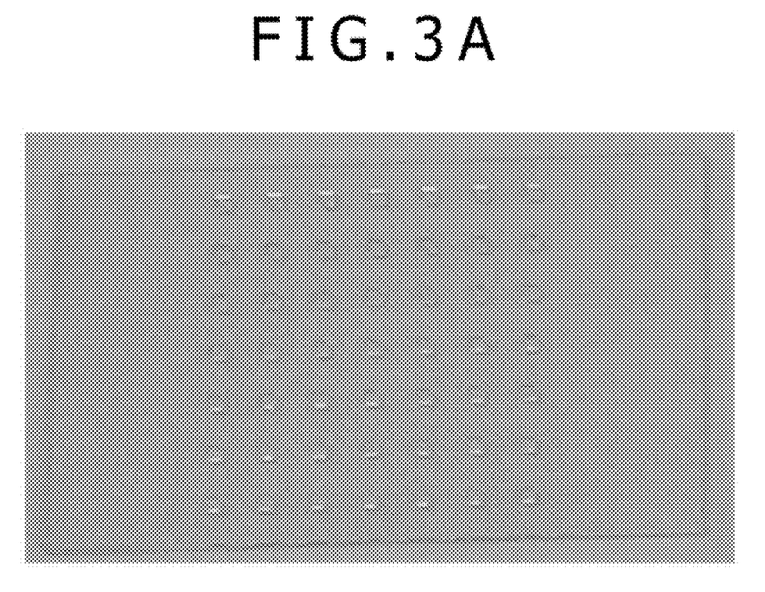
FIGS. 3A and 3B are respectively a view showing a test substrate before deposition of a DLC thin film in Example 1, and a view showing the test substrate after the deposition of the DLC thin film in Example 1.
Figure 3B:
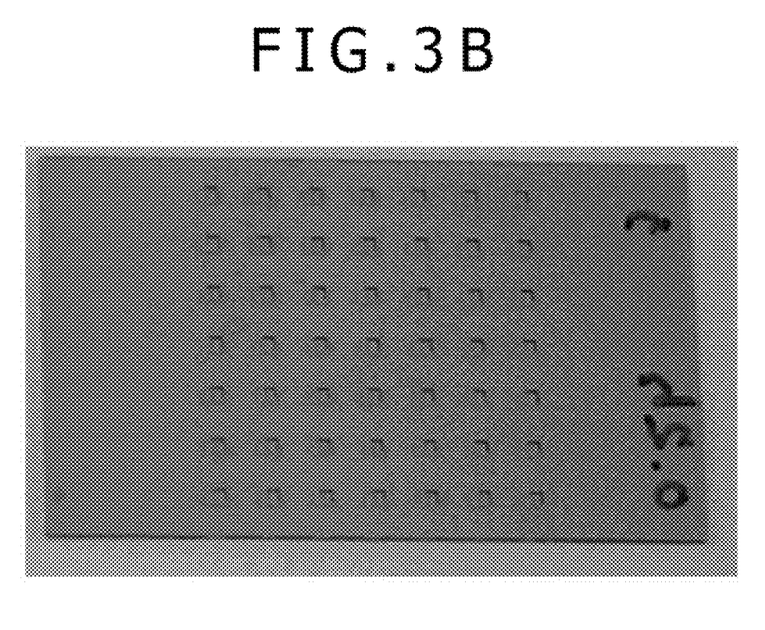

FIGS. 3A and 3B show the results of the test for depositing the DLC thin film. Here, FIG. 3A shows the test substrate before the film deposition, and FIG. 3B shows the test substrate after the film deposition.

In the DLC-covered test substrate on which the DLC thin film was deposited (refer to FIG. 3B), the DLC thin film was uniformly formed over the entire surface of the test substrate. In addition, it was confirmed that the DLC thin film can be formed on each of bottom surfaces as well of the wells each having a depth of 0.2 mm.

Example 2

2. Analysis of Composition of DLC Thin Film

In Example 2, in addition to the DLC thin film deposited in the film deposition test carried out in Example 1, a DLC thin film containing therein fluorine was deposited. Also, compositions of both the DLC thin films were analyzed by using a Fourier transform infrared spectrophotometer. In the deposition of the DLC thin film containing therein fluorine, $C_6F_6$ was used as the raw material gas under the deposition conditions described in Example 1.

The measurement of the Fourier Transform Infrared Spectroscopy (FT-IR) was carried out by utilizing an Attenuated Total Deflection (ATR) method, and by using NICOLET 8700 manufactured by Thermo Fisher Scientific Inc.

Figure 4:
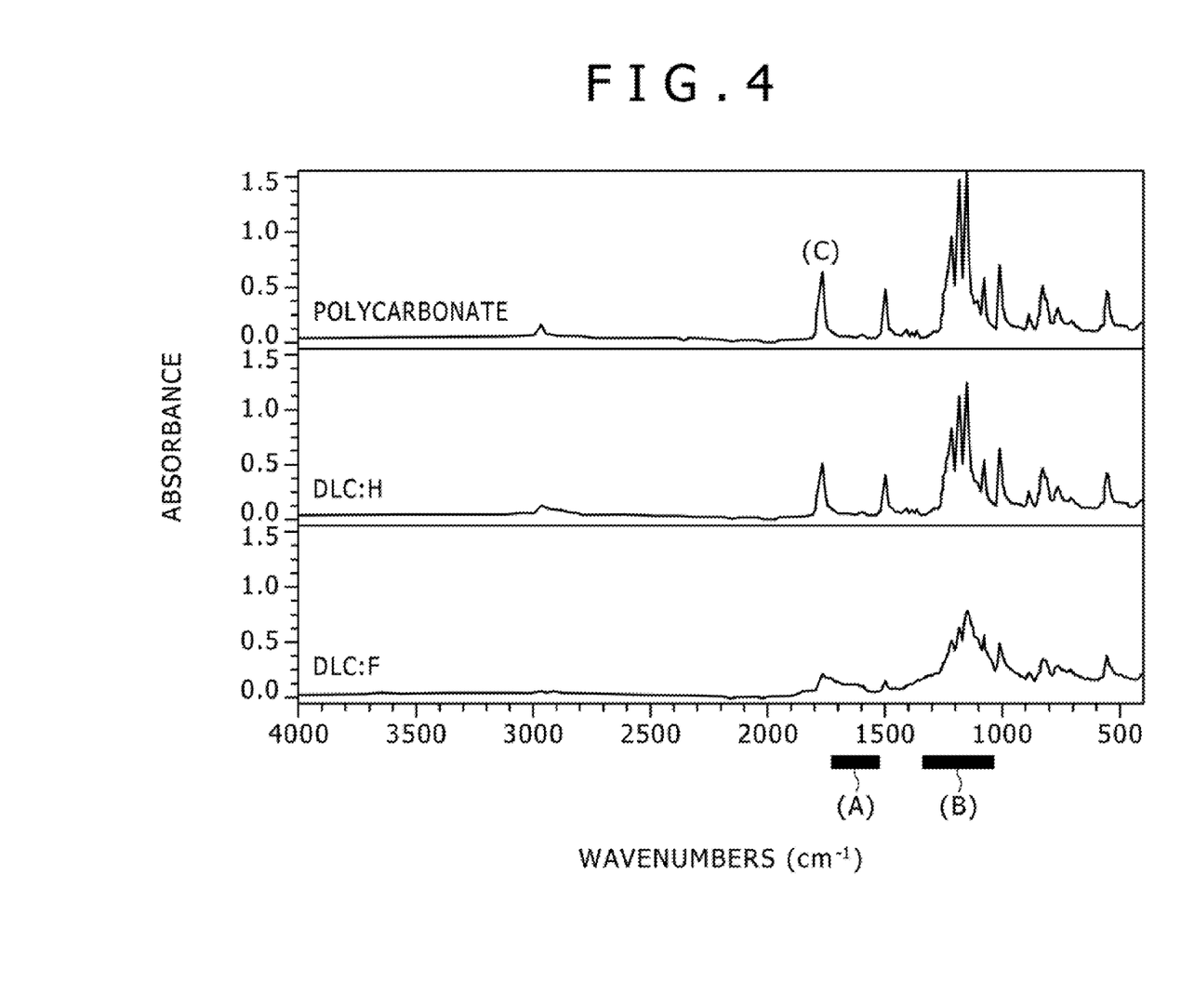
FIG. 4 is a spectrograph showing results of measuring Fourier-transform infrared spectroscopic spectra for a test substrate, DLC: H and DLC: F in Example 2.

FIG. 4 shows the results of the composition analysis. In the figure, "DLC: F" represents an ATR-FT-IR spectrum of the DLC thin film containing therein fluorine. "DLC: H" represents an ATR-FT-IR spectrum of the DLC thin film containing no fluorine. Also, "Polycarbonate" shows a result of the measurement made for the test substrate before the film deposition for comparison with each of "DLC: F" and "DLC: H".

In the ATR-FT-IR spectrum of the DLC thin film containing therein fluorine (hereinafter referred to as "DLC: F"), an absorption peak peculiar to a bond (Alkyl-Hal) of a carbon atom and a halogen atom appears in a wavenumber region indicated by reference symbol (A). In addition, an absorption peak (>C=C<) peculiar to a double bond between carbon atoms appears in a wavenumber region indicated by reference symbol (B).

An absorption peak indicated by reference symbol (C) is a spectrum based on a vibration made of a double bond (C=O) of a carbon atom and an oxygen atom. This absorption peak is observed in all the ATR-FT-IR spectra obtained in the experimental measurements. This is because a C=O bond within polycarbonate ester was detected since a polycarbonate ester plate was used as the polycarbonate plate. A chemical formula of polycarbonate ester is expressed as follows:

The adsorption peaks of the Alkyl-Hal bond and the >C=C< bond exist in the ATR-FT-IR spectrum of DLC: F. Thus, the absorption peak of the C=O bond is detected at a relatively smaller level than that of each of these absorption peaks.

On the other hand, although small reduction of the adsorption rate is observed in the ATR-FT-IR spectrum of the DLC thin film containing no fluorine (hereinafter referred to as "DLC: H"), the ATR-FT-IR spectrum of DLC: H is substantially identical to that of the polycarbonate plate. This shows that since the DLC thin film is transparent in the infrared region, the absorption in the polycarbonate substrate as the base was measured. That is to say, this represents that a thin film given brown and shown in FIG. 3B is the DLC thin film. Although the DLC is inactive for the infrared spectroscopy, it can be identified by utilizing the Raman spectroscopy which will be described later.

It was confirmed from the above experimental results that the thin films having the desired compositions, respectively, can be formed in DLC: F and DLC: H, respectively.

Example 3

3. Measurement of Contact Angle

In Example 3, the hydrophobric property was carried out for DLC: H and DLC: F deposited under the film deposition conditions described in Example 1 and Example 2. The evaluation of the hydrophobric property for DLC: H and DLC: F was carried out by measuring a contact angle for purified water by using a contact angle measurement device (dropmaster DM300 manufactured by Kyowa Interface Science Co., Ltd.).

Figure 5:
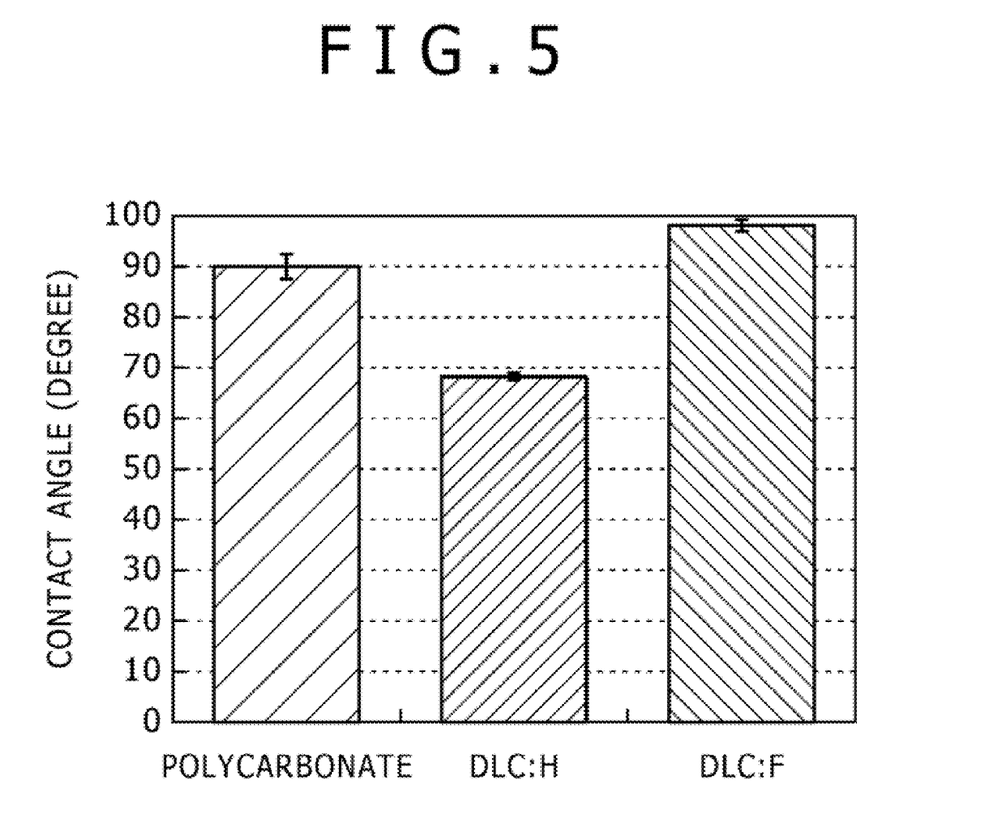
FIG. 5 is a graph showing results of measuring a contact angle for purified water on a substrate covered with DLC: H and a substrate covered DLC: F in Example 3.

FIG. 5 shows results of measuring the contact angle.

The contact angle with respect to the test substrate (polycarbonate test substrate) before the film deposition (indicated by "Polycarbonate" in the figure) was 90°, and the contact angle with respect to the polycarbonate substrate covered with DLC: H was 68°.

On the other hand, the contact angle with respect to the polycarbonate substrate covered with DLC: F was 98°, and thus increased as compared with each of the polycarbonate substrate covered with DLC: H and the test polycarbonate substrate before the film deposition.

It was confirmed from the above experimental results that by containing fluorine in the DLC thin film, the wettability of the DLC thin film for the water can be controlled, and the high hydrophobic property can be obtained.

Example 4

4. Investigation about Optical Transparency

In Example 4, the evaluation of the optical transparency (degree of coloring) was carried out for the substrate covered with DLC: H deposited under the film deposition conditions described in Example 1.

Figure 6A:
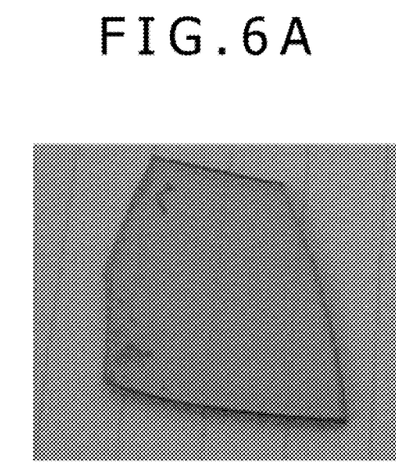
FIGS. 6A, 6B and 6C are respectively views showing an optical transparency of the substrate covered with the DLC thin film when film deposition is carried out while a film deposition time is changed in Example 4.
Figure 6B:
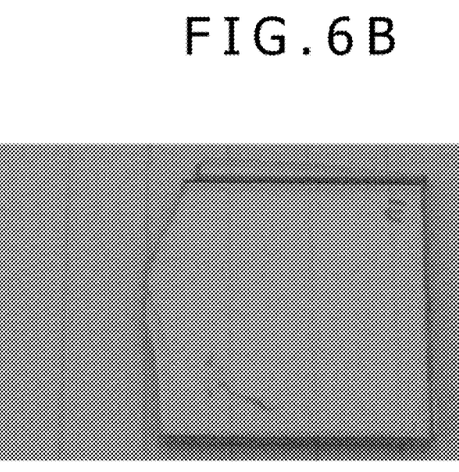
Figure 6C:
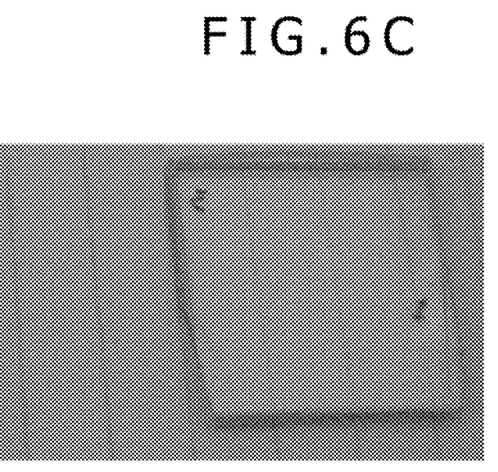

FIGS. 6A, 6B and 6C respectively show the polycarbonate substrates each of which is covered with DLC: H, i.e., on which the DLC thin film was deposited while the thin film deposit on time is changed under the film deposition conditions described in Example 1. Here, FIG. 6A shows the polycarbonate substrate covered with DLC: H formed in Example 1 (the film deposition time was 15 min.), FIG. 6B shows the polycarbonate substrate which is covered with DLC: H, i.e., on which the DLC thin film was deposited for a reduced time of 5 min., and FIG. 6C shows the polycarbonate substrate which is covered with DLC: H, i.e., on which the DLC thin film was deposited for a reduced time of 1 min.

It is understood from the above experimental results that the optical transparency of the polycarbonate substrate covered with the DLC thin film (the degree of coloring) can be controlled by controlling the thickness of DLC: H while the film deposition time is changed.

Example 5

5. Measurement about $SP^2/SP^3$

The DLC is composed of the $SP^3$ bond (diamond bond) and the $SP^2$ bond (graphite bond). The optical transparency of the DLC thin film can be controlled by adjusting the hybrid ratio, $SP^2/SP^3$, of the number of $SP^2$ bonds to the number of $SP^3$ bonds. In Example 5, the hybrid ratio $SP^2/SP^3$ was tried to be adjusted by changing the film deposition conditions.

The DLC: H was deposited while the accelerating voltage was changed under the film deposition conditions described in Example 1, and the hybrid ratio $SP^2/SP^3$ was measured for the resulting DLC: H by utilizing the Raman spectroscopy. The measurement of the Raman spectrum was carried out by using a microscopical laser Raman spectrometer, Lab RAM, manufactured by JOBIN YVON CO., LTD.

Figure 7A:
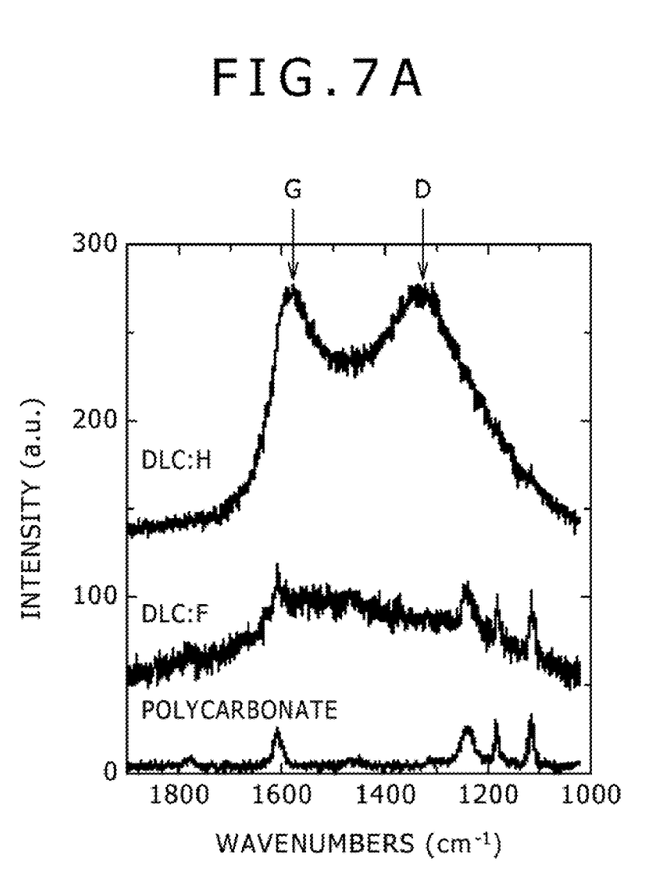
FIGS. 7A and 7B are respectively graphs obtained as results of measuring a hybrid ratio $SP^2/SP^3$ in Example 5.
Figure 7B:
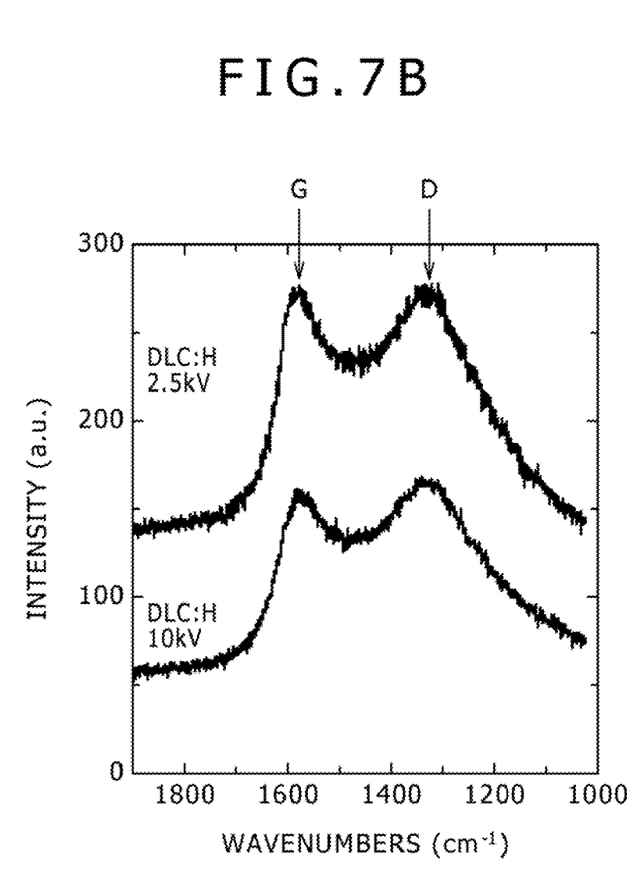

FIGS. 7A and 7B show the results of measuring the hybrid ratio $SP^2/SP^3$. In these figures, a Raman peak (G-peak) with a wavenumber of 1,560 $cm^{-1}$ indicated by reference symbol G is a peak due to the $SP^2$ bond. Also, a Raman peak (D-peak) with a wavenumber of 1,360 $cm^{-1}$ indicated by reference symbol D is a peak due to the $SP^3$ bond.

As shown in FIG. 7A, in the Raman peaks in DLC: H, a peak ratio between the G-peak and the D-peak is approximately equal to each other. On the other hand, in the Raman peaks in DLC: F, the G-peak is high (the hybrid ratio $SP^2/SP^3$ is high). From this fact, it is understood that the DLC thin film obtained by film deposition has a carbon skeleton.

FIG. 7B shows the Raman spectrum of DLC: H which is deposited when the accelerating voltage is changed so as to be set at 2.5 kV and at 10 kV. From the experimental results shown in FIG. 7B, it is understood that the hybrid ratio $SP^2/SP^3$ can be changed by changing the accelerating voltage.

Example 6

6. Measurement about Optical Transmittance

In Example 6, the measurement about the optical transmittance of the polycarbonate substrate covered with DLC: H manufactured under the film deposition conditions described in Example 1 was carried out.

Figure 8:
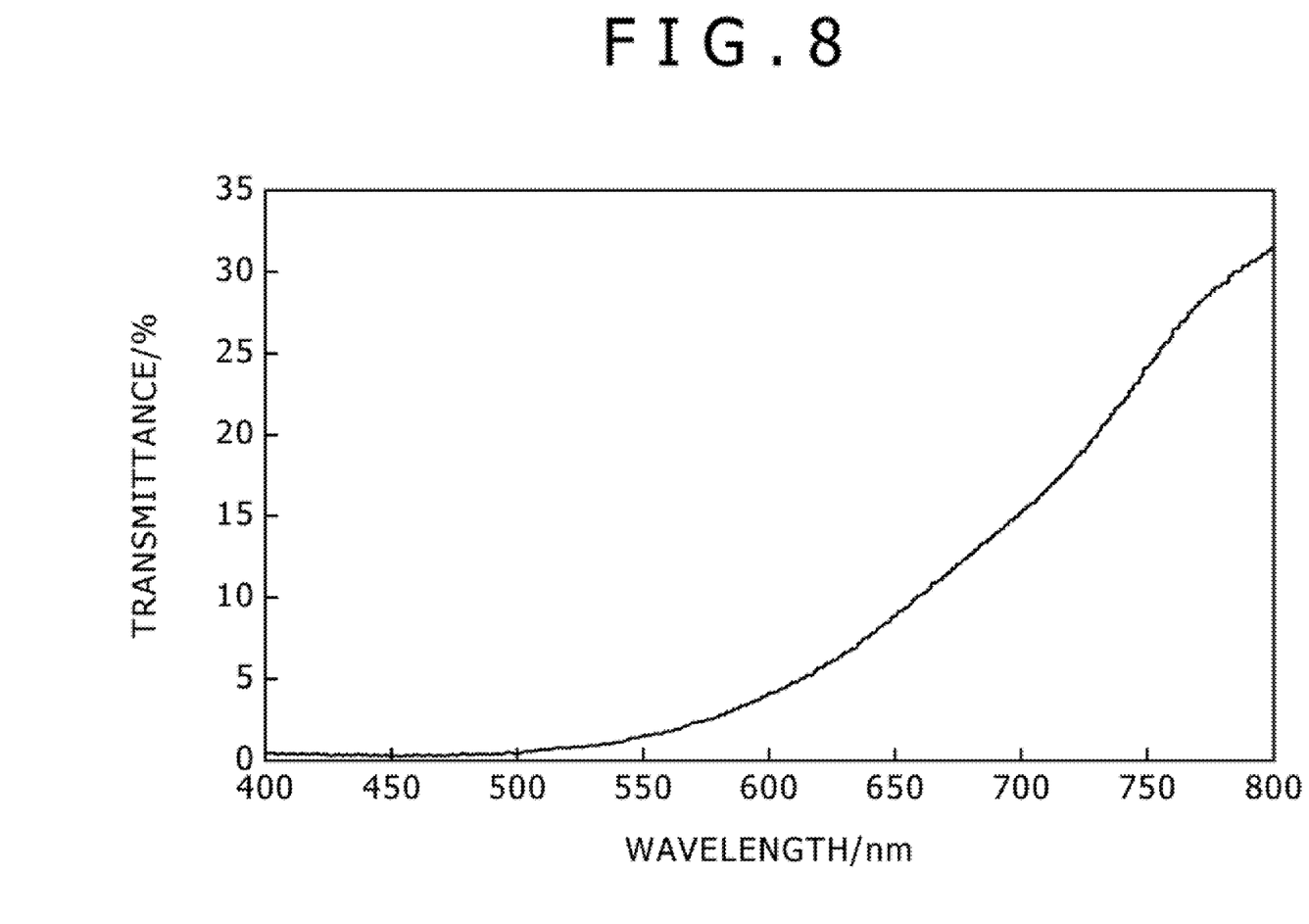
FIG. 8 is a graph obtained as results of measuring an optical transmittance of the substrate covered with DLC: H in Example 6.

FIG. 8 shows a transmission spectrum measured by using a spectrometer MCPD-7000 manufactured by OTSUKA ELECTRONICS CO., LTD. In the figure, an axis of abscissa represents a wavelength of a radiation light, and an axis of ordinate represents an optical transmittance.

As shown in the figure, the optical transmittance of the polycarbonate substrate covered with DLC: H was remarkably reduced to 10% or less in a visible light region of 400 to 600 nm.

Example 7

7. Measurement about Auto-Fluorescence Intensity and S/N Ratio

In Example 7, the investigation was carried out about the effect of suppression of the auto-fluorescence, and the effect of enhancement of the S/N ratio in the substrate covered with DLC: H manufactured under the film deposition conditions described in Example 1.

Figure 9A:
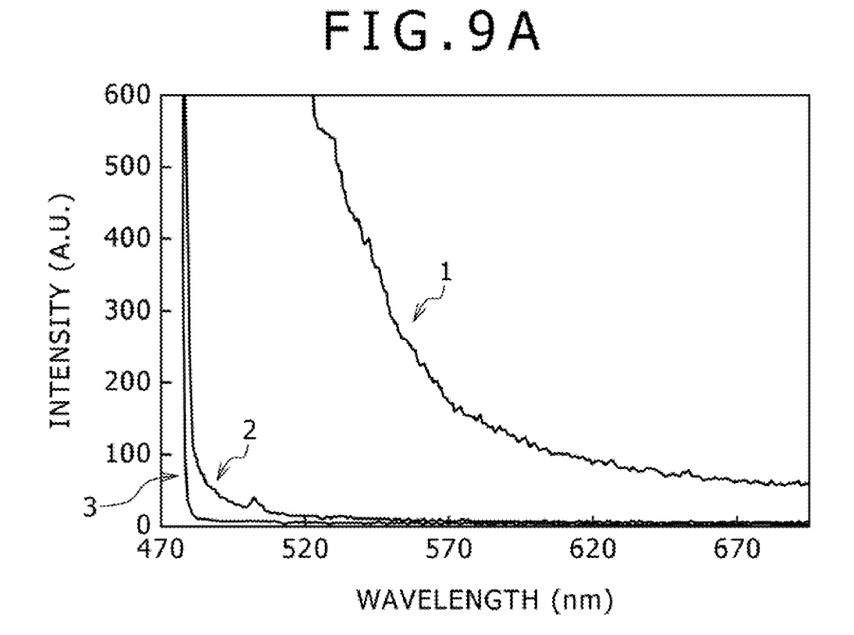
FIGS. 9A and 9B are respectively spectrographs showing results of measuring an auto-fluorescence intensity of the substrate covered with DLC: H in Example 7.
Figure 9B:
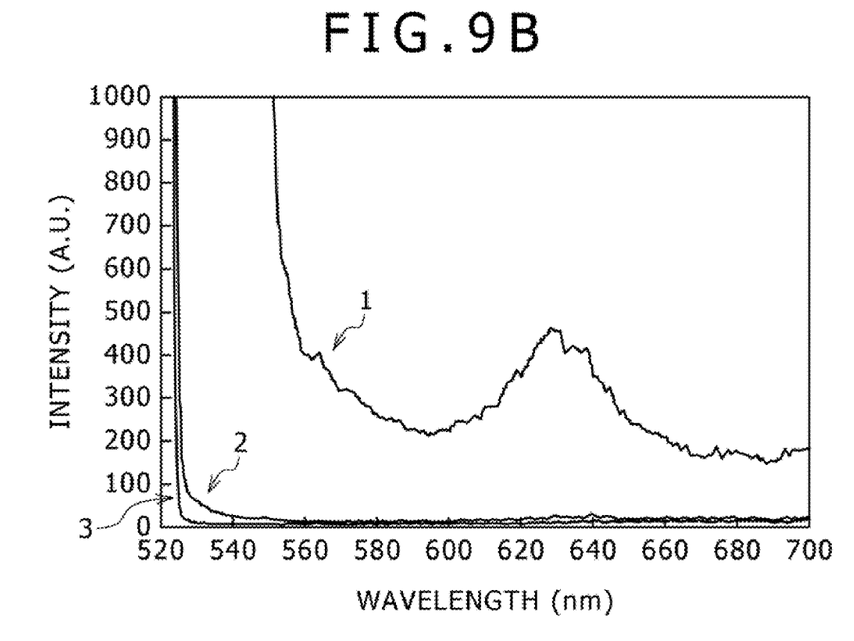

FIGS. 9A and 9B show the intensities of the auto-fluorescences measured by using a fluorescence spectrophotometer, FL-4500, manufactured by HITACHI CO., LTD. Here, FIG. 9A shows the results of radiating an excitation light having a given wavelength of 473 nm to the substrate covered with DLC: H, and measuring an intensity of a fluorescence from the substrate covered with DLC: H. Also, FIG. 9B shows the results of measuring an intensity of a fluorescence having a given wavelength of 520 nm when the wavelength of the excitation light is changed from 520 up to 700 nm.

In these figures, reference numeral 1 designates an auto-fluorescence from the test substrate (having no DLC: H) made of polypropylene having a strong auto-fluorescence property. In the substrate (designated by reference numeral 2) obtained by covering this polypropylene substrate covered with DLC: H, it is understood that the fluorescence intensity in the periphery of the detection wavelength is reduced to suppress the auto-fluorescence from the polypropylene substrate covered with DLC: H. Thus, covering the polypropylene substrate covered with DLC: H results in that the intensity of the auto-fluorescence from the resulting polypropylene substrate can be reduced to the same degree as that of an intensity of an auto-fluorescence (refer to reference numeral 3) from the polycarbonate substrate having the low auto-fluorescence property.

Next, 50 nL of the reaction liquid solution containing therein a reagent for the real-time PCR (SYBER Green Master Mix: Applied Biosystems) after completion of the PCR reaction was dispensed into each of the wells of the polypropylene substrate covered with DLC: H. Also, the fluorescence from the intercalator was observed by using a fluorescence microscope. A fluorescence image was acquired by using a cooled CCD camera, and the fluorescence intensity was quantified in image processing.

Figure 10A:
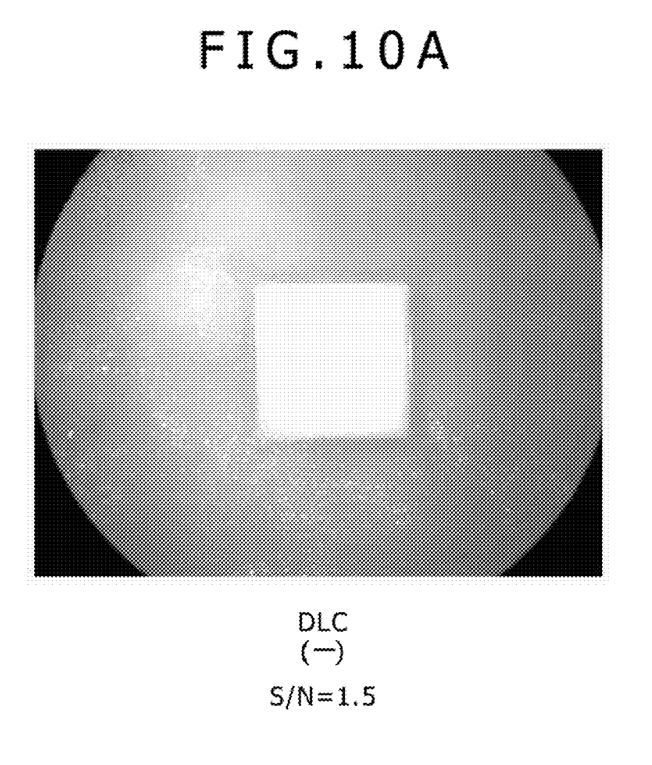
FIGS. 10A and 10B are respectively views showing results of measuring an S/N ratio of the substrate covered with DLC: H in Example 7.
Figure 10B:
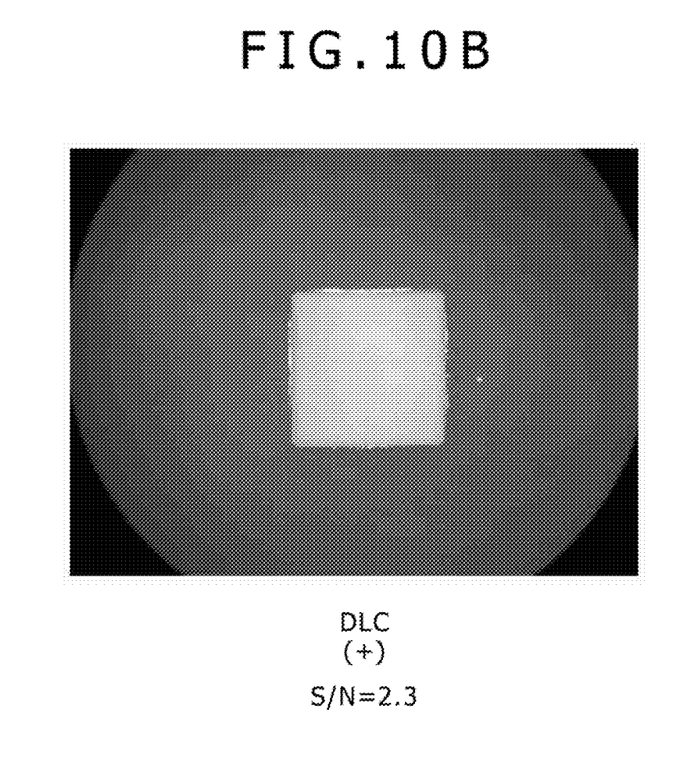

FIGS. 10A and 10B respectively show images observed by using the fluorescence microscopy. Here, FIG. 10A is a fluorescence image of the polypropylene substrate before the film deposition of DLC: H, and FIG. 10B is a fluorescence image of the well in the polypropylene substrate covered with DLC: H. In these figures, a square image located at a central portion is a well image. It is observed that the well glows a white color owing to the fluorescence from the intercalator in the inside of the well.

In the polypropylene substrate before the film deposition of DLC: H shown in FIG. 10A, it is observed that the substrate region located outside the well also glows a white color owing to the auto-fluorescence property of the polypropylene substrate. For this reason, the S/N ratio (the fluorescence intensity in the well/the fluorescence intensity in the outside of the well) shows a low value of 1.5. On the other hand, in the polypropylene substrate covered with DLC: H shown in FIG. 10B, it is understood that the luminescence in the substrate region located outside the well is suppressed, and thus only the fluorescence due to the intercalator within the well is observed. As a result, in this case, the S/N ratio is increased up to 2.3.

It was confirmed from the above experimental results that the detection sensitivity can be enhanced by about 50%.

Example 8

8. Test for Impeding Adsorption of Nucleic Acid

In Example 8, the evaluation of an amount of nucleic acid adsorbing on the surface was carried out for each of the polycarbonate substrate covered with DLC: H, and the polycarbonate substrate covered with DLC: F made under the conditions described in Example 1 and Example 2.

In the case of the polycarbonate substrate covered with DLC: F, DLC: F was deposited on the polycarbonate substrate under the conditions that the raw material gas was $C_6F_6$, the accelerating voltage was set at 2.5 kV, and the R.F power was set at 500 W. On the other hand, in the case of the polycarbonate substrate covered with DLC: H, DLC: H was deposited on the substrate under the conditions that the raw material gas was toluene, the accelerating voltage was set at 2.5 kV, and the R.F power was set at 500 W. For comparison with each of polycarbonate substrate covered with DLC: F, and the polycarbonate substrate covered with DLC: H, the polycarbonate substrate before the film deposition was used. 20 μL of Cy3-labeled DNA (20 mer, 10 μM) was put on each of the surfaces of the substances, and was stationarily left at a room temperature for 90 min. Next, each of the substrates was immersed in a HEPES Buffer, and was cleaned in a shaker at 150 rpm for five min. Thereafter, each of the substrates was rinsed with MilliQ water, the fluorescence image of DNA-Cy3 adsorbing on each of the surfaces of the substrates was acquired by using the fluorescence microscope, and each of the fluorescence intensities was quantified in the image processing.

Figure 11:
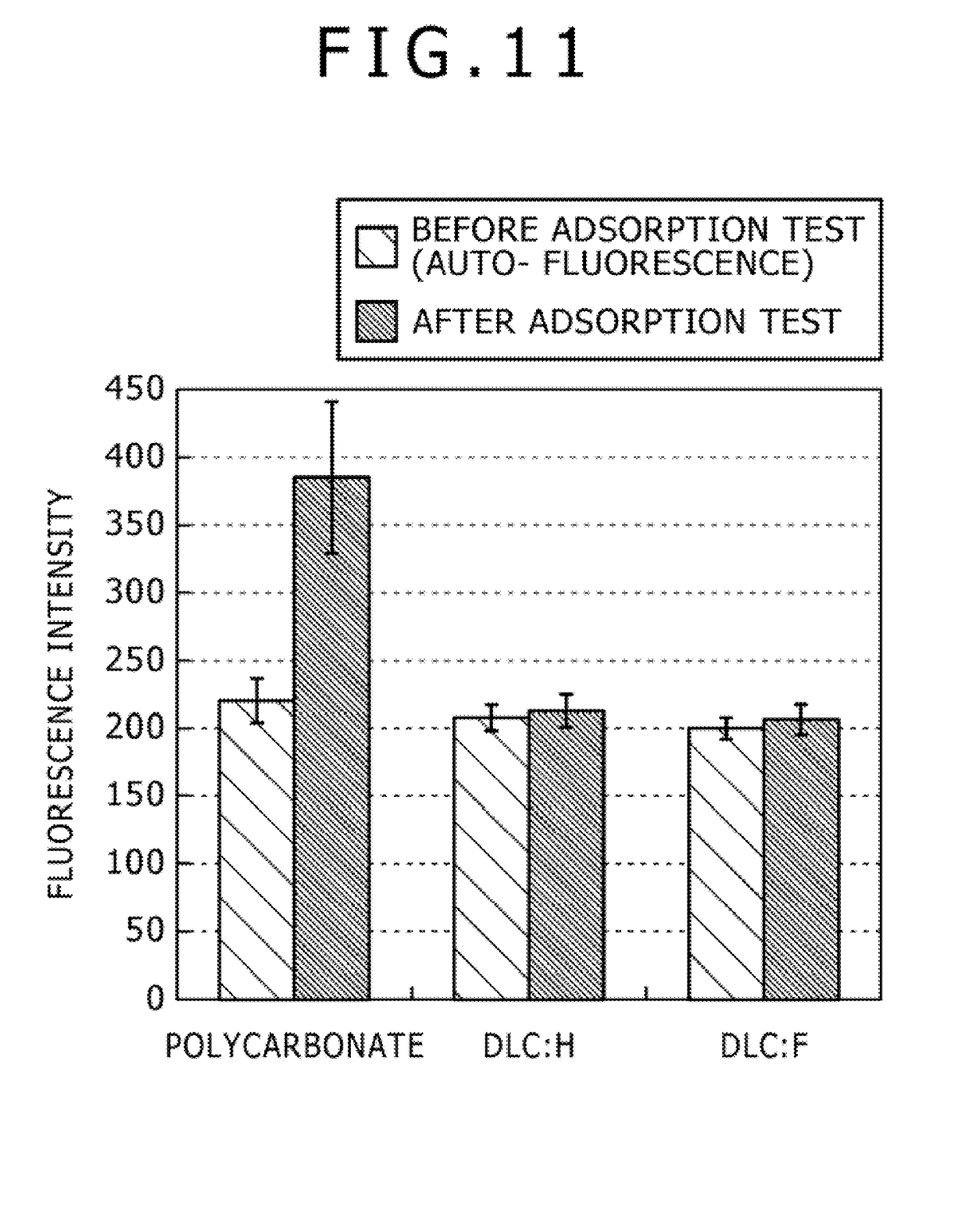
FIG. 11 is a graph showing results of a test for nucleic acid adsorption on the substrate covered with DLC: H and the substrate covered with DLC: F in Example 8.

FIG. 11 shows the results of measurements of the intensities of the fluorescences from these substrates. As shown in the figure, in the polycarbonate substrate before the film deposition, the adsorption of the Cy3-labeled DNA on the surface of the polycarbonate substrate approximately doubled the fluorescence intensity. On the other hand, in each of the polycarbonate substrate covered with DLC: H, and the polycarbonate substrate covered with DLC: F, it is understood that the increase in fluorescence intensity is suppressed, and thus the adsorption of the nucleic acid on each of the surfaces of these substrates is remarkably suppressed.

The optical detection field according to the present invention can be used for optically detecting the various substances. For example, the optical detection field is adopted suitably in the substrate for the real-time PCR, the DNA chip and the like.

It should be understood by those skilled in the art that various modifications, combinations, sub-combinations and alterations may occur depending on design requirements and other factors insofar as they are within the scope of the appended claims or the equivalents thereof.

What is claimed is:

1. An optical detection field, comprising:
    a reaction region, of a plurality of reaction regions, wherein,
        the reaction region is configured to facilitate a fluorsecent reaction of at least one substance,
        a diamond-like carbon thin film containing therein fluorine is formed on a surface of the reaction region, such that the film is between the surface of the reaction region and the substance, the film has a transmittance of visibile light of 10% or less, the film contains therein flourine in atom ratio (F/(F+C+H)) of 0 to 40%, the film has a hybrid ratio of $SP^2/SP^3$ set in the range of 0.5 to 1.1, and the film has a thickness set in the range of 1 to 1,000 nm, and
        the reaction region is adjacent to a cover that is opposite the film, such that the substance is between the thin film and the cover, and the cover is optically transparent over the range of wavelengths that the reaction fluoresces.

2. The optical detection field according to claim 1, further comprising:
    a flow channel configured to:
        introduce the substance to the reaction region, of the plurality of reaction regions, and
        discharge the substance from the reaction region, of the plurality of reaction regions,
    wherein said diamond-like carbon thin film is formed on a surface of said flow channel, such that the diamond-like thin film is between the surface of the flow channel and the substance.

3. The optical detection field according to claim 2, wherein said optical detection field is used for detection of fluorescence substance in a real-time Polymerase Chain Reaction-or a Deoxyribo Nucleic Acid chip.

* * * * *